US008868209B2

(12) United States Patent
Clark et al.

(10) Patent No.: US 8,868,209 B2
(45) Date of Patent: Oct. 21, 2014

(54) FIXATION MECHANISMS FOR TEMPORARY IMPLANTABLE MEDICAL ELECTRICAL STIMULATION LEADS

(71) Applicant: Cardiac Pacemakers, Inc., St. Paul, MN (US)

(72) Inventors: Bryan A. Clark, Forest Lake, MN (US); Timothy R. Jackson, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/031,013

(22) Filed: Sep. 18, 2013

(65) Prior Publication Data

US 2014/0081363 A1   Mar. 20, 2014

Related U.S. Application Data

(60) Provisional application No. 61/702,819, filed on Sep. 19, 2012.

(51) Int. Cl.
*A61N 1/00* (2006.01)
*A61N 1/05* (2006.01)
*A61N 1/36* (2006.01)

(52) U.S. Cl.
CPC .............. *A61N 1/05* (2013.01); *A61N 1/36007* (2013.01); *A61N 2001/058* (2013.01); *A61N 1/0558* (2013.01)
USPC .............................. 607/116; 607/37; 607/127

(58) Field of Classification Search
USPC ........................................... 607/37, 116, 127
See application file for complete search history.

(56) References Cited

U.S. PATENT DOCUMENTS

| 6,104,960 | A | 8/2000 | Duysens et al. |
|---|---|---|---|
| 6,129,751 | A | 10/2000 | Lucchesi et al. |
| 7,881,783 | B2 | 2/2011 | Bonde et al. |
| 2007/0179582 | A1* | 8/2007 | Marshall et al. ............... 607/119 |
| 2007/0250143 | A1 | 10/2007 | Sommer |
| 2007/0255366 | A1 | 11/2007 | Gerber et al. |
| 2007/0255369 | A1 | 11/2007 | Bonde et al. |
| 2007/0255370 | A1 | 11/2007 | Bonde et al. |
| 2010/0268310 | A1 | 10/2010 | Bonde et al. |
| 2011/0257500 | A1* | 10/2011 | Wells et al. .................... 600/373 |
| 2014/0031661 | A1 | 1/2014 | Clark et al. |

OTHER PUBLICATIONS

International Search Report and Written Opinion issued in PCT/US2013/060483, mailed Feb. 17, 2014.
Partial International Search Report (from Invitation to Pay Additional Fees) issued in PCT/US2013/060483, Nov. 22, 2013.
Second Written Opinion issued in PCT/US2013/060483 on Aug. 25, 2014, 6 pages.

* cited by examiner

*Primary Examiner* — Nicole F Lavert
(74) *Attorney, Agent, or Firm* — Faegre Baker Daniels LLP

(57) ABSTRACT

A temporary implantable medical device lead includes a connector configured to connect the lead to an external control module, a helically coiled conductor including a plurality of insulated filars and having a proximal end mechanically and electrically connected to the connector, and one or more electrodes defined by uninsulated portions of the helically coiled conductor. The temporary implantable medical device lead also includes one or more tine assemblies proximal to the one or more electrodes and configured to inhibit axial migration of the temporary implantable medical device lead, each tine assembly including a base and a plurality of tines extending from the base.

21 Claims, 7 Drawing Sheets

FIXATION MECHANISMS FOR TEMPORARY IMPLANTABLE MEDICAL ELECTRICAL STIMULATION LEADS

CROSS-REFERENCE TO RELATED APPLICATION

This application claims the benefit of Provisional Application No. 61/702,819, filed Sep. 19, 2012, which is incorporated herein by reference in its entirety.

TECHNICAL FIELD

The present disclosure relates to implantable medical leads. More particularly, the present disclosure relates to fixation mechanisms for temporary implantable medical leads.

BACKGROUND

Temporary implantable medical leads may be used to evaluate the efficacy of stimulation (e.g., neurostimulation) prior to implanting chronically implantable systems within a patient. For example, as a treatment for urinary incontinence, patients may be implanted with a trial percutaneous nerve evaluation (PNE) lead to evaluate the efficacy of sacral nerve stimulation.

Temporary leads may migrate, potentially causing the lead to lose the ability to deliver effective therapy. As a result, higher non-responder rates can occur in patients receiving the temporary lead compared to patients receiving a permanent pacing lead to evaluate the efficacy of stimulation.

SUMMARY

Disclosed herein are fixation mechanisms for inhibiting axial migration of temporary implantable medical device leads, as well as temporary implantable leads including such fixation mechanisms.

In Example 1, a temporary implantable medical device lead includes a connector configured to connect the lead to an external control module, a helically coiled conductor including a plurality of insulated filars and having a proximal end mechanically and electrically connected to the connector, and one or more electrodes defined by uninsulated portions of the helically coiled conductor. The temporary implantable medical device lead also includes one or more tine assemblies proximal to the one or more electrodes and configured to inhibit axial migration of the temporary implantable medical device lead, each tine assembly including a base and a plurality of tines extending from the base.

In Example 2, the temporary implantable medical device lead according to Example 1, wherein a first outer diameter of the helically coiled conductor adjacent to each of the one or more tine assemblies is less than a second outer diameter of the helically coiled conductor along portions not adjacent to the one or more tine assemblies.

In Example 3, the temporary implantable medical device lead according to Example 2, wherein a difference between the second outer diameter and the first outer diameter is up to twice a thickness of the one or more tines.

In Example 4, the temporary implantable medical device lead according to any of Examples 1-3, wherein at least one of the one or more tine assemblies is configured to prevent distal axial migration of the temporary implantable medical device lead.

In Example 5, the temporary implantable medical device lead according to any of Examples 1-4, and further comprising one or more insulative filars co-radial with the helically coiled conductor, wherein the base of each of the one or more tine assemblies is bonded to the one or more insulative filars.

In Example 6, the temporary implantable medical device lead according to any of Examples 1-5, and further comprising a distal tine assembly disposed at a distal end of the helically coiled conductor distal to the one or more electrodes and configured to inhibit radial movement of the lead.

In Example 7, the temporary implantable medical device lead according to any of Examples 1-6, wherein the helically coiled conductor includes one or more preformed sections that are collapsible during implantation and that increase an outer diameter of the temporary implantable medical device lead after implantation.

In Example 8, the temporary implantable medical device lead according to Example 7, and further comprising one or more electrodes on each of the one or more preformed sections.

In Example 9, the temporary implantable medical device lead according to Example 7, and further comprising a distal lead cap coupled to a distal end of the helically coiled conductor, wherein the distal lead cap includes a cup or slot configured to receive an implantation tool to collapse the preformed section during implantation.

In Example 10, the temporary implantable medical device lead according to any of Examples 1-9, and further comprising a shape memory element coextending with a portion of the helically coiled conductor, the shape memory element collapsible to a position adjacent to the helically coiled conductor during implantation and expandable to a diameter greater than an outer diameter of the helically coiled conductor after implantation.

In Example 11, a temporary implantable medical device lead includes a connector configured to connect the lead to an external control module and a helically coiled conductor including a plurality of insulated filars having a proximal end mechanically and electrically connected to the connector. The helically coiled conductor also includes one or more preformed sections that are collapsible during implantation and that increase an outer diameter of the temporary implantable medical device lead after implantation. The temporary implantable medical device lead also includes one or more electrodes defined by uninsulated portions of the helically coiled conductor.

In Example 12, the temporary implantable medical device lead according to Example 11, and further comprising a distal lead cap coupled to a distal end of the helically coiled conductor, wherein the distal lead cap includes a cup or slot configured to receive an implantation tool to collapse the preformed section during implantation.

In Example 13, the temporary implantable medical device lead according to either Example 11 or Example 12, wherein at least one of the one or more preformed sections comprises a flare in the helically coiled conductor.

In Example 14, the temporary implantable medical device lead according to any of Examples 11-13, and further comprising one or more electrodes on each of the one or more preformed sections.

In Example 15, the temporary implantable medical device lead according to any of Examples 11-14, and further comprising one or more tine assemblies configured to inhibit axial migration of the temporary implantable medical device lead, each tine assembly including a base and a plurality of tines extending from the base, wherein a first outer diameter of the helically coiled conductor adjacent to each of the one or more tine assemblies is less than a second outer diameter of the helically coiled conductor along portions not adjacent to the one or more tine assemblies.

In Example 16, the temporary implantable medical device lead according to Example 15, wherein a difference between the second outer diameter and the first outer diameter is up to two times a thickness of the one or more tines.

In Example 17, the temporary implantable medical device lead according to either Example 15 or Example 16, wherein at least one of the one or more tine assemblies is configured to prevent distal axial migration of the temporary implantable medical device lead.

In Example 18, a system includes an externally carried control module and a temporary implantable medical device lead. The temporary implantable medical device lead includes a connector configured to connect the lead to the control module, a helically coiled conductor including a plurality of insulated filars and having a proximal end mechanically and electrically connected to the connector, and one or more electrodes defined by uninsulated portions of the helically coiled conductor. The temporary implantable medical device lead also includes one or more tine assemblies proximal to the one or more electrodes and configured to inhibit axial migration of the temporary implantable medical device lead, each tine assembly including a base and a plurality of tines extending from the base.

In Example 19, the system according to Example 18, wherein a first outer diameter of the helically coiled conductor adjacent to each of the one or more tine assemblies is less than a second outer diameter of the helically coiled conductor along portions not adjacent to the one or more tine assemblies.

In Example 20, the system according to Example 19, wherein a width between the second outer diameter and the first outer diameter is up to two times a thickness of the one or more tines.

In Example 21, the system according to any of Examples 17-20, wherein at least one of the one or more tine assemblies is configured to prevent distal axial migration of the temporary implantable medical device lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
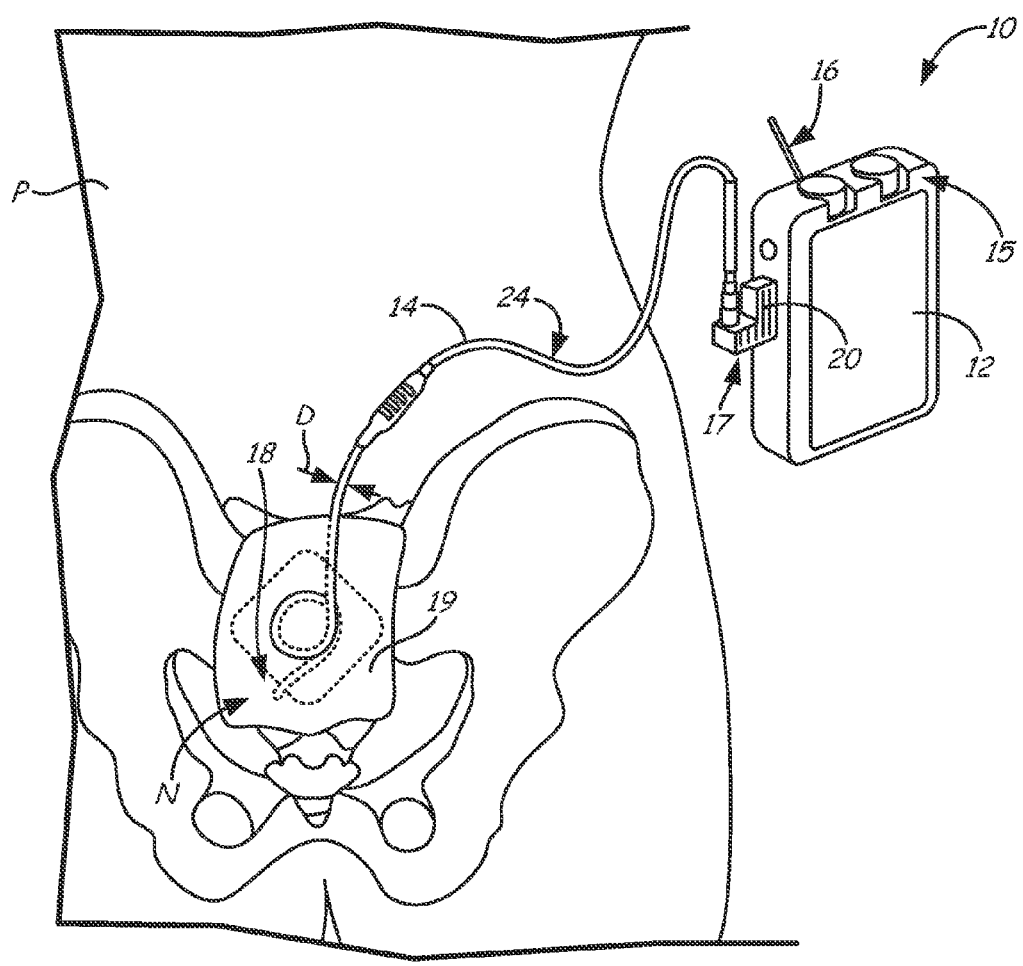
FIG. 1 illustrates an embodiment of an implantable multipolar temporary lead positioned proximate the sacral nerves of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an embodiment of an electrical stimulation system 10 including a control module (e.g., stimulator or pulse generator) 12 and a temporary implantable medical device lead 14 coupled to the control module 12. In some embodiments, the electrical stimulation system 10 is a peripheral nerve evaluation (PNE) stimulation system, which allows temporary implantation of a lead at a nerve site to test whether neurostimulation at the site improves the condition being treated. In the embodiment shown, the lead 14 is implanted proximate a sacral nerve N of a patient P. In other embodiments, the electrical stimulation system 10 is configured to provide stimulation to other nerve bundles or other portions or systems of the body. While illustrated and described as a temporary lead, the lead 14 may alternatively be configured as a chronically implanted lead.

The control module 12 is configured to deliver stimulation signals to the lead 14 and/or receive electrical signals sensed by the lead 14. In some embodiments, the control module 12 is an externally carried or worn device. The control module 12 may include external controls 15 that allow the clinician to set characteristics (e.g., periodicity, frequency, amplitude, etc.) of the therapy delivered to the sacral nerve N via the lead 14. The control module 12 may also include an antenna 16 configured to communicate with an external device (e.g., programmer), for example to receive programming related to therapy delivery.

The lead 14 includes a proximal end 17 and a distal end 18. In some embodiments, the distal end 18 of the lead 14 includes a plurality of electrodes (not shown) positioned proximate to the sacral nerve N. The lead 14 may be introduced from the posterior side of the sacrum, through a foramen thereof, and into the region of the sacral nerves and positioned such that a plurality of electrodes at the distal end 18 is in close vicinity to the sacral nerve N for electrical stimulation. At the percutaneous entry site on the back of the patient P, the lead 14 may be coiled and affixed to the skin with a temporary dressing 19. At the proximal end 17, the lead includes a connector 20 configured to mechanically and electrically couple the lead 14 to the control module 12. The connector 20 may include a plurality of contacts that electrically couple the electrodes at the distal end 18 of the lead 14 to the electrical components of the control module 12 via a conductor extending through the lead 14.

The conductor extending through the lead 14 can be a helically coiled multifilar conductor. As used herein, a filar may be a single conductive wire or a cable comprising a plurality of bundled wires. The multifilar conductor is electrically connected to the control module 12 such that different wires of the conductor are capable of carrying different electrical signals for stimulation of the sacral nerve N. In some embodiments, the multifilar conductor is electrically insulated with a layer of insulating material that surrounds each filar. In some embodiments, the insulative layer can be removed from an uninsulated portion of each of the filars near the distal end 18. The uninsulated portion of each of the filars is exposed at an exterior of the body of the lead 14 such that the exposed uninsulated portions of the filars define the plurality of electrodes at longitudinally spaced sections along a distal region near the distal end of the lead 14.

With a plurality of electrodes, the lead 14 according to the present disclosure is configured for multipolar stimulation, thereby eliminating the ground pad used in unipolar PNE systems. In addition, the multiple electrodes at the distal end 18 of the lead 14 improves the likelihood that therapeutic stimulation of the sacral nerve N is consistently delivered during the evaluation period, due to the number of electrodes disposed in proximity to the sacral nerve N. That is, even if the lead 14 migrates during the evaluation period and one of the electrodes at the distal end 18 moves away from the sacral nerve N, other electrodes at the distal end 18 may remain in close proximity to the sacral nerve N after the migration.

In some embodiments, the lead 14 has a relatively small outer diameter D. In some embodiments, the outer diameter D is less than about 0.05 inch (1.27 mm). For example, in some embodiments, the outer diameter is less than about 0.025 inch (0.635 mm). The outer diameter D may be such that the lead 14 can be implanted using a small diameter needle having a lumen diameter corresponding to the outer diameter D. For example, in some embodiments, the needle used for implantation of the lead 14 may be a 16 gauge or 20 gauge foramen needle.

In some embodiments, the outer surface of the lead 14 is defined by the insulated and uninsulated filars of the lead conductor. In alternative embodiments, the lead 14 may include a lead body 24 that covers the lead conductor. Portions of the lead body 24 at the location of uninsulated portions of the lead conductor at the distal end 18 may be removed to expose the electrodes at an exterior of the lead body 24. In some embodiments, the lead body 24 is comprised of an insulative material, such as, for example, ethylene tetrafluoroethylene (ETFE), polytetrafluoroethylene (PTFE), parylene, other fluoropolymers, silicone, polyurethane, polyester, or rubber. In alternative embodiments, the lead 14 does not include an insulative lead body 24.

Figure 2:
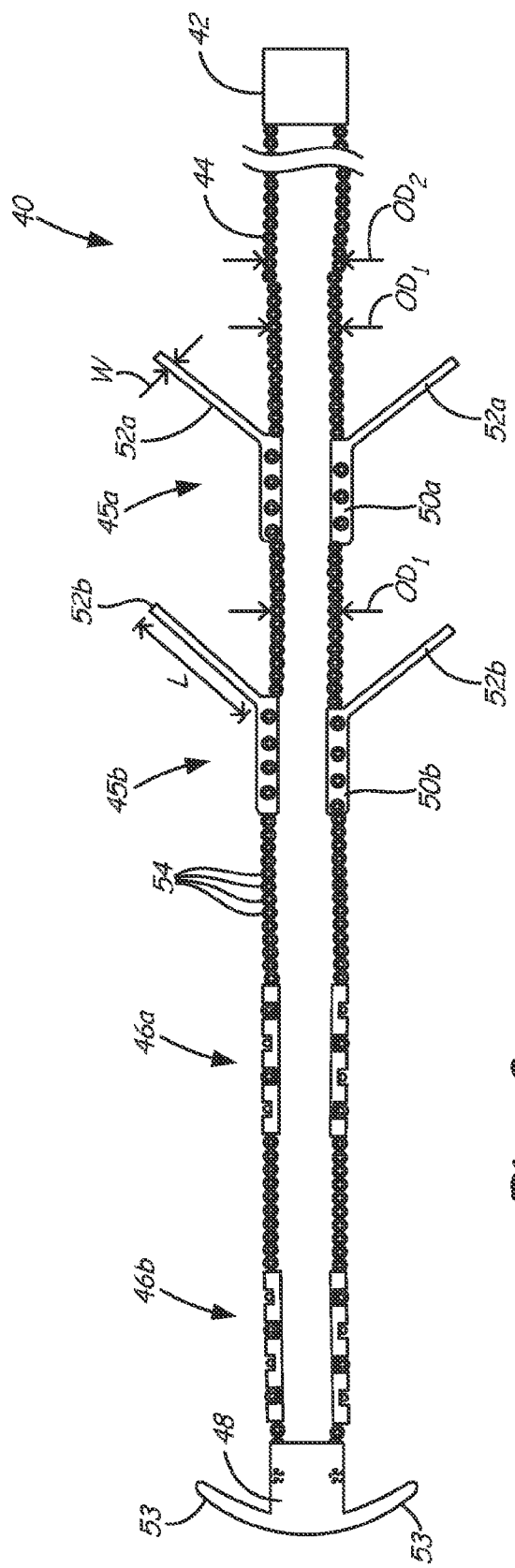
FIGS. 2-5 are schematic cross-sectional views of implantable temporary leads including stabilizing tines according to embodiments of the present disclosure.

FIG. 2 is a schematic cross-sectional view of a temporary implantable medical device lead 40 according to an embodiment of the present disclosure. The lead 40 includes a connector 42 at a proximal end of the lead configured to interface with a device configured to deliver signals to the lead 40 (e.g., control module 12). The lead 40 also includes a conductor 44, tine assemblies 45a and 45b, electrodes 46a and 46b, and a distal tine assembly 48. The tine assembly 45a includes a base 50a and tines 52a, and the tine assembly 45b includes a base 50b and tines 52b. The distal tine assembly 48 includes tines 53.

The conductor 44 is mechanically and electrically connected to the connector 42 and extends distally therefrom. The conductor 44 includes a plurality of insulated filars 54. In one exemplary embodiment, the conductor includes four filars 54. However, the conductor 44 may include any number of filars 54. For example, in other embodiments, the conductor 44 includes two to eight filars. The conductive portion of the filars 54 may be comprised of a conductive material such as, for example, stainless steel, MP35N, platinum, platinum-iridium, or tantalum.

The filars 54 are each coated circumferentially with an insulative material, which electrically isolates the filars 54 from each other. In some embodiments, the insulative material is comprised of a material such as, for example, ETFE, PTFE, parylene, silicone, or polyurethane, although other insulative materials are also possible. In some embodiments, the insulative material on each of the filars 54 is comprised of the same insulative material. In alternative embodiments, the insulative material differs between some of the filars 54.

The diameter of each of the filars 54 may be less than about 0.006 inch (0.152 mm), and a thickness of the insulative material may be less than about 0.002 inch (0.051 mm). In some embodiments, the thickness of the insulative material is in the range of about 0.00025 inch to about 0.001 inch (0.006-0.025 mm). The filars 54 are closely wound such that the spacing between adjacent turns of the conductor 42 is less than about 0.005 inch (0.127 mm). In some embodiments, the spacing between adjacent turns of the filars 54 is less than about 0.001 inch (0.025 mm).

In various embodiments, the insulative layer is removed from sections of the filars 54 near the distal end of the lead 40 to define a plurality of longitudinally spaced electrodes 46a and 46b. For example, the insulative layer may be removed from sections of the filars 54 via an ablation process. The uninsulated portions of the filars 54 define the electrodes 46a, 46b. In the embodiment illustrated, the electrodes 46a, 46b are disposed at the outer surface of the conductor 42 to form a substantially constant outer diameter. Additional exemplary embodiments of electrodes for the leads described herein are illustrated and described in U.S. Prov. Patent App. No. 61/675,407, entitled "Temporary Implantable Medical Electrical Stimulation Lead," which is hereby incorporated by reference in its entirety.

The tine assemblies 45a, 45b and distal tine assembly 48 are configured to inhibit axial migration of the lead 40 after implantation. Particularly, the tines 52a extend from the base 50a, the tines 52b extend from the base 50b, and the tines 53 extend from the distal tine assembly 48. When implanted, the tines 52a, 52b, and 53 interface with tissue or other body structures to prevent axial movement of the lead 40 (i.e., in the direction of the longitudinal axis of the lead 40). In addition, the distal tine assembly 48 may be configured to limit or inhibit radial movement of the distal end of the lead 40 after implantation. In some embodiments, the tines 52a, 52b, and/or 53 extend from the lead 40 at an angle between about 10° and about 45°. In other embodiments, the angle of the tines 52a, 52b, and/or 53 with respect to the lead 40 is greater than 45°.

During implantation, the tines 52a, 52b, and 53 are urged against an outer surface of the conductor 44 and fed through an implantation needle or catheter. To minimize the outer diameter of the lead 40 (and accommodate the lumen sizes of standard implantation needles or catheters), the conductor 44 may include a region adjacent to the tine assemblies 45a, 45b and/or distal tine assembly 48 having a smaller diameter to accommodate the tines 52a, 52b, and/or 53 when urged against the conductor 44. These regions may be sized such that the overall outer profile of the lead 40 during implantation is substantially constant. For example, in the illustrated embodiment, the conductor 44 includes an outer diameter $OD_1$ adjacent to the tine assemblies 45a, 45b that is less than an outer diameter $OD_2$ not adjacent to the tine assemblies 45a, 45b. Also, in the embodiment shown, the diameter of the base of the distal tine assembly is less than the outer diameter $OD_2$ to accommodate the tines 53 during implantation. In some embodiments, the difference between the outer diameter $OD_2$ and the outer diameter $OD_1$ is up to twice a thickness or width w of the tines 52a, 52b. In other embodiments, the difference between the outer diameter $OD_2$ and the outer diameter $OD_1$ is approximately equal to the width w (or diameter) of the tines 52a, 52b. In addition, the length of the conductor having the outer diameter $OD_1$ may be approximately equal to a length L of the tines 52a, 52b. In some embodiments, the width w of each of the tines 52a, 52b, and 53 is less than about 0.010 inch (0.254 mm) and the length of each of the tines is between about 0.0313 inch and 0.125 inch (0.794-3.18 mm).

In alternative embodiments, the conductor 44 has a substantially constant diameter along a length of the lead 40.

The tine assemblies 45a, 45b, and 48 may include any number of tines 52, 52b, and 53 in any type of orientation. In one exemplary embodiment, the tine assemblies 45a, 45b, and/or 48 include one tine. In another exemplary embodiment the tine assemblies 45a, 45b, and/or 48 include two tines separated circumferentially by between 5° and 180°. In a further exemplary embodiment, the tine assemblies 45a, 45b, and/or 48 include three tines separated circumferentially by between 5° and 170°. In a still further exemplary embodiment, the tine assemblies 45a, 45b, and/or 48 include four tines separated circumferentially by between 5° and 165°. While the embodiments of the tine assemblies 45a, 45b, and 48 have been described as including one to four tines, other embodiments including a greater number of tines are also contemplated. In addition, the tines 52a, 52b, and 53 may be circumferentially aligned with each other along the length of the lead 40, or the tines 52a, 52b, and 53 may be circumferentially offset or staggered with respect to each other.

The tine assemblies 45a, 45b and distal tine assembly 48 may be secured to the conductor 44 in a variety of ways. In the embodiment illustrated, the bases 50a and 50b are overmolded with the filars 54 of the conductor 44 proximal to the electrodes 46a, 46b, and the distal tine assembly 48 is overmolded with the filars 54 at the distal end of the conductor 44 distal to the electrodes 46a, 46b. In some embodiments, the pitch of the conductor 44 along the portion overmolded with the tine assemblies 45a, 45b, and 48 is greater than or equal to the pitch of the conductor 44 along other portions of the lead 40. With a greater pitch, the material of the tine assemblies 45a, 45b, and 48 can flow between the turns of the conductor 44 to strengthen the mechanical attachment of the tine assemblies 45a, 45b, and 48 to the conductor 44. The tine assemblies 45a, 45b and/or distal tine assembly 48 may alternatively be secured to the conductor 44 using alternative means, such as adhesives, thermal fusion, and mechanical attachment means. In some embodiments, the tine assemblies 45a, 45b and the distal tine assembly 48 are comprised of a flexible biocompatible polymeric material, such as silicone, polyurethane, polyisobutylene-based polyurethane, fluoropolymers, copolymers, and combinations and blends thereof.

Figure 3:
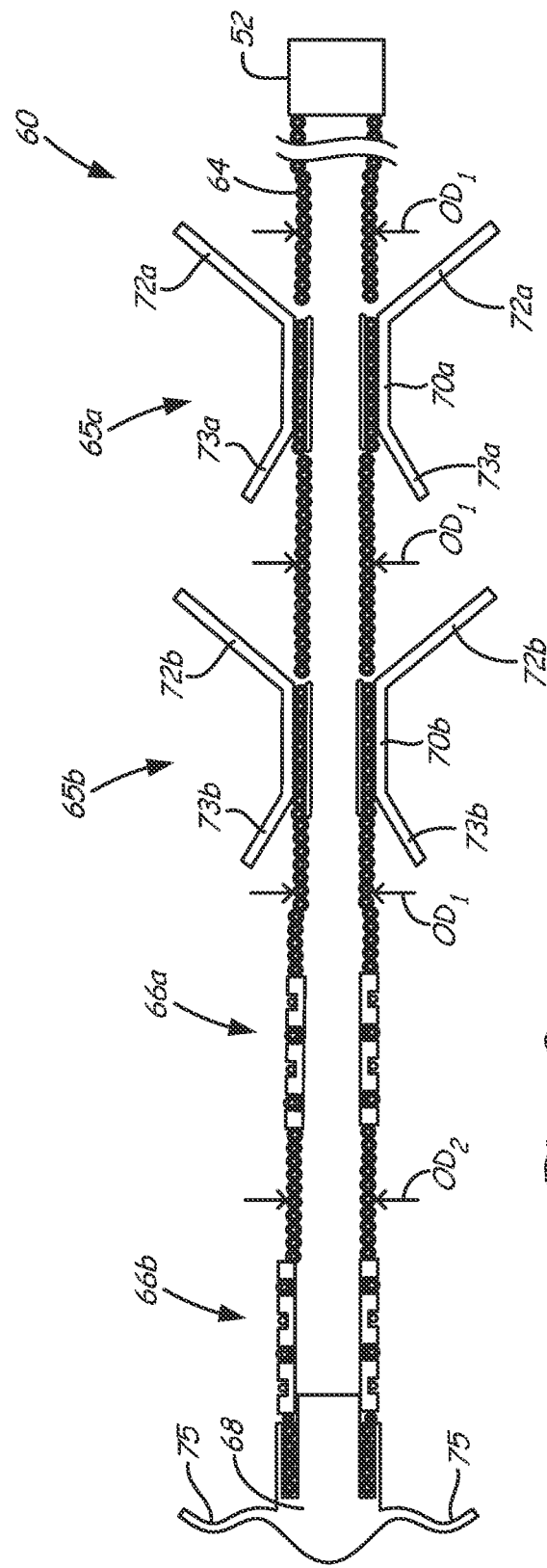

FIG. 3 is a schematic cross-sectional view of a temporary implantable medical device lead 60 according to another embodiment of the present disclosure. The lead 60 includes a connector 52 at a proximal end of the lead configured to interface with a device configured to deliver signals to the lead 60 (e.g., control module 12). The lead 60 also includes a conductor 64, tine assemblies 65a and 65b, electrodes 66a and 66b, and a distal tine assembly 68. The tine assembly 65a includes a base 70a, proximal tines 72a, and distal tines 73a, and the tine assembly 65b includes a base 70b, proximal tines 72b, and distal tines 73b. The distal tine assembly 68 includes tines 75.

The connector 52, conductor 64, and electrodes 66a and 66b may have configurations and characteristics similar to the connector 42, conductor 44, and electrodes 46a and 46b, respectively, as described herein with regard to FIG. 2. In addition, the tine assemblies 65a, 65b and the distal tine assembly 68 may include tine numbers, arrangements, and materials similar to those described herein with regard to tine assemblies 45a, 45b, and distal tine assembly 48, respectively.

In the embodiment illustrated in FIG. 3, the tine assembly 65a includes proximal tines 72a and distal tines 73a extending from the base 70a, and the tine assembly 65b includes proximal tines 72b and distal tines 73b extending from the base 70b. The proximal tines 72a and 72b have characteristics similar to those of tines 52a and 52b described herein. The distal tines 73a and 73b are arranged and configured to prevent distal axial migration of the lead 60 after implantation. Particularly, the distal tines 73a and 73b are angled to interface with tissue or other body structures to prevent movement of the lead 60 in a direction away from the proximal end.

In addition the distal tine assembly 68 includes tines 75 that are configured to limit or inhibit axial movement of the lead 60 in both the proximal and distal directions, as well as prevent or reduce radial movement of the distal end of the lead. In the illustrated embodiment, the tines 75 include a waved or undulating structure.

During implantation, the tines 72a, 72b, 73a, 73b, and 75 are urged against an outer surface of the conductor 64 and fed through an implantation needle or catheter. To minimize the outer diameter of the lead 60, the conductor 64 may include regions adjacent to the tine assemblies 65a, 65b and/or distal tine assembly 68 having a smaller diameter to accommodate the tines 72a, 72b, 73a, 73b, and/or 75 when urged against the conductor 64. These regions may be sized such that the overall outer profile of the lead 60 during implantation is substantially constant. For example, in the illustrated embodiment, the conductor 64 includes regions having an outer diameter $OD_1$ adjacent to the tine assemblies 65a, 65b that is less than an outer diameter $OD_2$ not adjacent to the tine assemblies 65a, 65b. Similar to the embodiment described in FIG. 2, in some embodiments, the difference between the outer diameter $OD_2$ and the outer diameter $OD_1$ is up to twice a thickness (or diameter) of the tines 72a, 72b, 73a, 73b. In addition, the length of the conductor having the outer diameter $OD_1$ may be approximately equal to a length of the tines 72a, 72b, 73a, 73b. With particular reference to the embodiment illustrated in FIG. 3, the length of the portion of the conductor 64 between the tine assemblies 65a, 65b having the outside diameter $OD_1$ is approximately equal to the combined length of the distal tines 73a of the tine assembly 65a, and the proximal tines 72b of the tine assembly 65b.

The tine assemblies 65a, 65b and distal tine assembly 68 may be secured to the conductor 64 in a variety of ways. In the embodiment illustrated, the bases 70a and 70b each include an inner lumen substrate that is joined to the remainder of the bases 70a, 70b across the conductor 64. Similarly, the distal tine assembly 68 includes an inner lumen portion that is joined to an outer portion of the distal tine assembly 68 across the conductor 64 (e.g., via thermal fusion). In some embodiments, the pitch of the conductor 64 along the portion mechanically coupled with the tine assemblies 65a, 65b, and 68 is greater than or equal to the pitch of the conductor 64 along other portions of the lead 60. With a greater pitch, the material of the tine assemblies 65a, 65b, and 68 can flow between the turns of the conductor 64 to strengthen the mechanical attachment of the tine assemblies 65a, 65b, and 68 to the conductor 64. The tine assemblies 65a, 65b and/or distal tine assembly 68 may alternatively be secured to the conductor 64 using alternative means, such as adhesives, overmolding, and mechanical attachment means.

Figure 4:
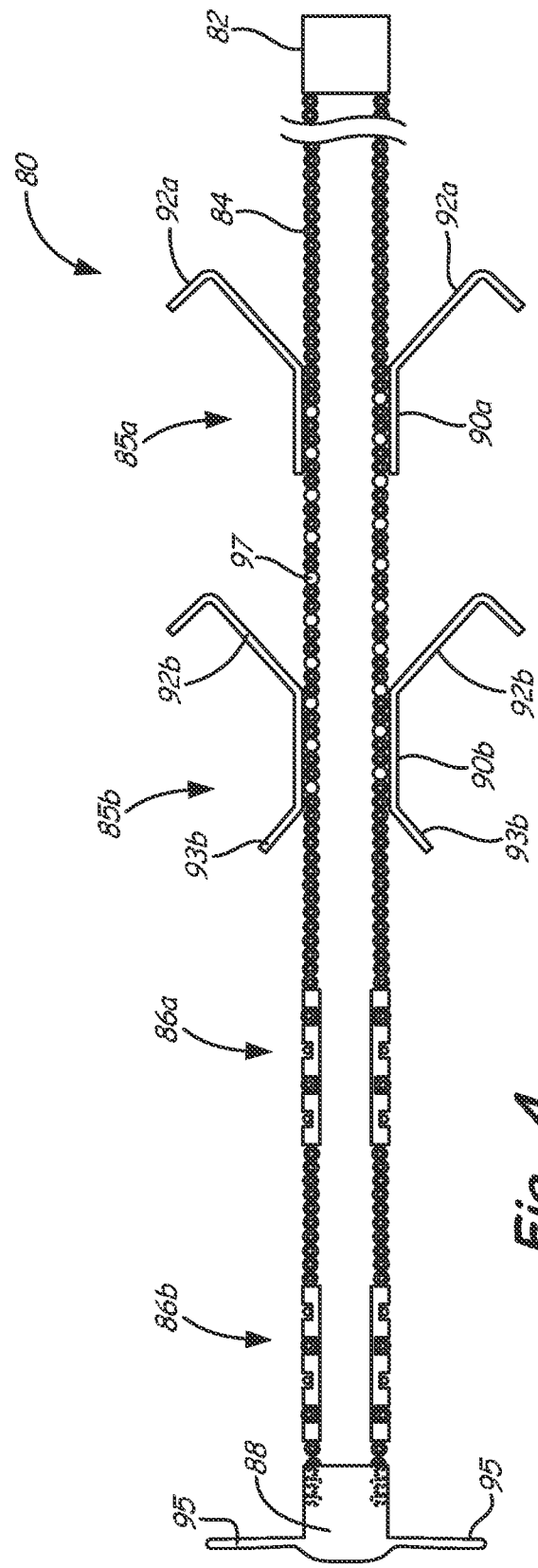

FIG. 4 is a schematic cross-sectional view of a temporary implantable medical device lead 80 according to another embodiment of the present disclosure. The lead 80 includes a connector 82 at a proximal end of the lead configured to interface with a device configured to deliver signals to the lead 80 (e.g., control module 12). The lead 80 also include a conductor 84, tine assemblies 85a and 85b, electrodes 86a and 86b, and a distal tine assembly 88. The tine assembly 85a includes a base 90a and proximal tines 92a, and the tine assembly 85*b* includes a base 90*b*, proximal tines 92*b*, and distal tines 93*b*. The distal tine assembly 88 includes tines 95.

The connector 82, conductor 84, and electrodes 86*a* and 86*b* may have configurations and characteristics similar to the connector 42, conductor 44, and electrodes 46*a* and 46*b*, respectively, as described herein with regard to FIG. 2. In addition, the tine assemblies 85*a*, 85*b* and the distal tine assembly 88 may include tine numbers, arrangements, and materials similar to those described herein with regard to tine assemblies 45*a*, 45*b*, and distal tine assembly 48, respectively. Further, while not specifically illustrated in FIG. 4, the conductor 84 may include sections with smaller diameters as described herein to accommodate the tines of the lead 80 during implantation such that the outer profile of the lead 80 is substantially constant or uniform.

The tine assembly 85*a* includes proximal tines 92*a* extending from the base 90*a*, and the tine assembly 85*b* includes proximal tines 92*b* and distal tines 93*b* extending from the base 90*b*. In the embodiment illustrated in FIG. 4, the proximal tines 92*a*, 92*b* each include a proximally extending portion and a distally extending portion. The proximally and distally extending portions of the proximal tines 92*a*, 92*b* are angled with respect to each other. In some embodiments, the angle between the proximally and distally extending portions is less than or equal to about 90°. In some embodiments, a length of the distally extending portions of the proximal tines 92*a*, 92*b* is less than about 0.0625 in (1.59 mm). The distally extending portions of the tines 92*a*, 92*b* are arranged and configured to prevent distal axial migration of the lead 80 after implantation.

The distal tines 93*b* have characteristics similar to distal tines 73*a*, 73*b* described herein. The distal tines 93*b* are also arranged and configured to prevent distal axial migration of the lead 80 after implantation. While only the tine assembly 85*b* is illustrated as including distal tines 93*b*, the tine assembly 85*a* may also include one or more distal tines.

In addition the distal tine assembly 88 includes tines 95 that are configured to limit or inhibit axial movement of the lead 80 in both the proximal and distal directions, as well as prevent or reduce radial movement of the distal end of the lead 80 after implantation. In the illustrated embodiment, the tines 95 are straight and extend substantially orthogonally from the body of the distal tine assembly 88.

The tine assemblies 85*a*, 85*b* and distal tine assembly 88 may be secured to the conductor 84 in a variety of ways. In the embodiment illustrated, one or more filars 97 are wound co-radially with the filars of the conductor 84 and serve as a bonding substrate for the tine assemblies 85*a* and 85*b*. Particularly, the bases 90*a* and 90*b* are positioned to surround or otherwise abut one or more filars 97, and the bases 90*a*, 90*b* are bonded (e.g, melted) to the one or more filars 97. In some embodiments, the one or more filars 97 comprise a polymeric material, such as polyurethane, which can be bonded or heat bonded to the bases 90*a*, 90*b*. In other embodiments, the filars 97 comprise of a metallic material that is not electrically active but provides a surface to which the bases 90*a*, 90*b* can be bonded. In further embodiments, the filars 97 comprise a polymer-coated metal, such as a polyurethane-coated metal, which is not electrically active and provides a polymeric surface to which the bases 90*a*, 90*b* can be bonded. The distal tine assembly 88 may be secured to the distal end of the conductor 84 using methods similar to those discussed herein with regard to the distal tine assembly 44. The tine assemblies 85*a*, 85*b* and/or distal tine assembly 88 may alternatively be secured to the conductor 84 using alternative means, such as adhesives, overmolding, and mechanical attachment means.

Figure 5:
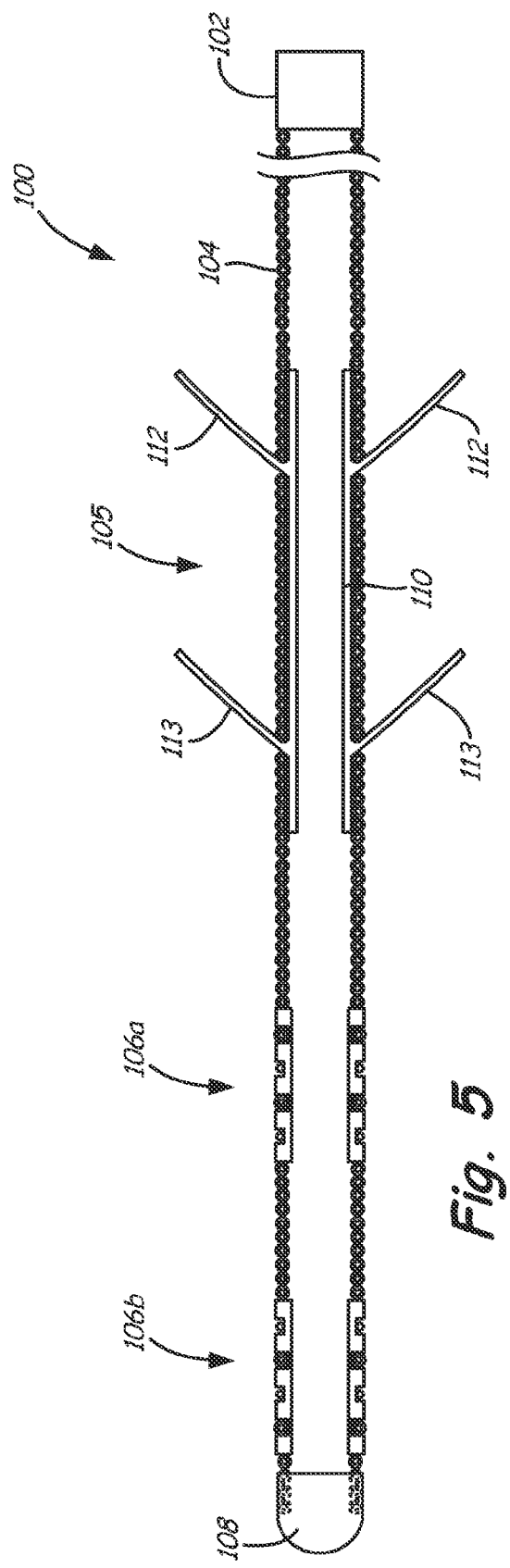

FIG. 5 is a schematic cross-sectional view of a temporary implantable medical device lead 100 according to another embodiment of the present disclosure. The lead 100 includes a connector 102 at a proximal end of the lead configured to interface with a device configured to deliver signals to the lead 100 (e.g., control module 12). The lead 100 also include a conductor 104, tine assembly 105, electrodes 106*a* and 106*b*, and a distal lead cap 108. The tine assembly 105 includes a base 110, proximal tines 112, and distal tines 113. The distal lead cap 108 is configured to facilitate traversal of the lead 100 to an implantation site, although the distal lead cap 108 may alternatively include one or more tines.

The connector 102, conductor 104, and electrodes 106*a* and 106*b* may have configurations and characteristics similar to the connector 42, conductor 44, and electrodes 46*a* and 46*b*, respectively, as described herein with regard to FIG. 2. In addition, the tine assembly 105 may include tine numbers, arrangements, and materials similar to those described herein with regard to tine assemblies 45*a*, 45*b*. Further, while not specifically illustrated in FIG. 5, the conductor 104 may include sections with smaller diameters as described herein to accommodate the tines of the lead 100 during implantation such that the outer profile of the lead 100 is substantially constant or uniform. In some embodiments, the conductor 104 includes areas of variable pitch to facilitate passing of the body of the tines 112, 113 between the filars.

The tine assembly 105 includes proximal tines 112 and distal tines 113 extending from the base 110. The tine assembly 105 may be secured to the conductor 104 in a variety of ways. In the embodiment illustrated, the base 110 extends though an inner lumen of the conductor 104, and the proximal tines 112 and distal tines 113 extend between turns of the conductor 104 to an exterior of the lead 110. In some embodiments, the tine assembly 105 is secured with respect to the conductor 104 due to the mechanical interaction between the base 110, tines 112, 113, and conductor 104. In other embodiments, the tine assembly 105 is additionally secured to the conductor via bonding (e.g., adhesive, epoxy, etc.) or fusing (e.g., thermal fusion, melting, etc.) the tine assembly 105 and conductor 104 together.

Figure 6:
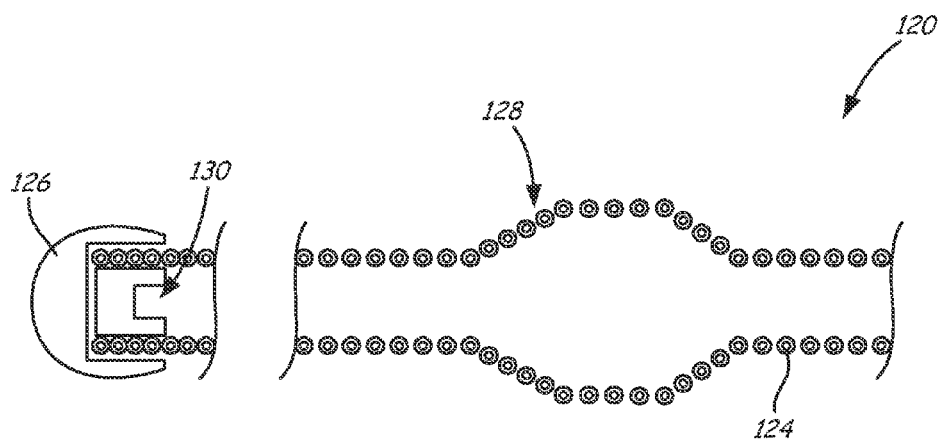
FIG. 6 is a schematic cross-sectional view of an implantable temporary lead including a conductive coil having a section that flares after implantation.

While the embodiments of the temporary implantable medical device lead have been described as including tines to prevent axial and/or radial movement of the lead, other fixation mechanisms are also possible to prevent movement after implantation. For example, FIG. 6 is a schematic cross-sectional view of a portion of a temporary implantable medical device lead 120 according to another embodiment of the present disclosure. The lead 120 includes a conductor 124 and a distal lead cap 126. While not specifically illustrated in FIG. 6, the lead 120 includes other elements similar to those described herein, such as a connector at the proximal end of the lead 120, and electrodes near a distal end of the lead 120.

The conductor 124 is configured to expand radially when the lead 120 is implanted. More particularly, the conductor 124 includes a flared section 128 that has an outer diameter greater than other portions of the conductor 124 along the length of the lead 120. When in the expanded state, the flared section 128 provides an outward radial force on surrounding tissue, thereby facilitating fixation of the lead 120. In some embodiments, the flared section 128 is formed by winding the conductor 124 around a mandrel or other device having a section with a larger diameter than the remainder of the mandrel. In some embodiments, the flared section 128 includes one or more electrodes.

During implantation, the flared section 128 is collapsed to provide a substantially uniform outer profile for the lead 120. In some embodiments, the conductor 124 is twisted or otherwise manipulated to collapse the flared section 128. In other embodiments, the lead 120 is stretched axially to collapse the flared section 128. For example, in the embodiment illustrated the lead 120 includes a distal lead cap 126 coupled to a distal end of the conductor 124. In some embodiments, the distal lead cap 126 includes a cup or slot 130 or other interface that mates with a stylet or other delivery device. The stylet may be manipulated to push the distal lead cap 126 distally to stretch the flared section 128 into the collapsed position or engage with the lead cap 126 and be rotated to collapse the flared section 128.

Figure 7:
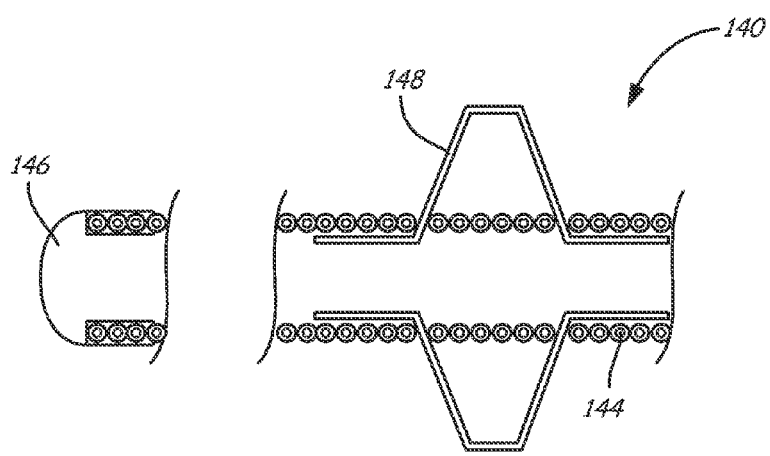
FIG. 7 is a schematic cross-sectional view of an implantable temporary lead including a shape memory component that flares after implantation.

FIG. 7 is a schematic cross-sectional view of a portion of a temporary implantable medical device lead 140 according to another embodiment of the present disclosure. The lead 140 includes a conductor 144 and a distal lead cap 146. While not specifically illustrated in FIG. 7, the lead 140 includes other elements similar to those described herein, such as a connector at the proximal end of the lead 140, and electrodes near a distal end of the lead 140.

The lead 140 further includes a shape memory element 148 coupled to the conductor 144 and configured to expand radially when the lead 140 is implanted. More particularly, shape memory element 148 has an outer diameter greater than the conductor 144 when the shape memory element 148 is in the expanded state. When in the expanded state, the shape memory element 148 provides an outward radial force on surrounding tissue, thereby facilitating fixation of the lead 140. In some embodiments, the shape memory element 148 is comprised of a polymeric or metal material. If the shape memory element 148 is formed of a conductive material, the shape memory element 148 may be configured to operate as an electrode.

During implantation, the shape memory element 148 is collapsed to provide a substantially uniform outer profile for the lead 140. In some embodiments, the lead 140 (and shape memory element 148) are stretched axially to collapse the shape memory element 148. For example, in the embodiment illustrated the lead 140 includes a distal lead cap 146 coupled to a distal end of the conductor 144. A stylet may be manipulated to push the distal lead cap 146 distally to stretch the shape memory element 148 into the collapsed position.

Figure 8:
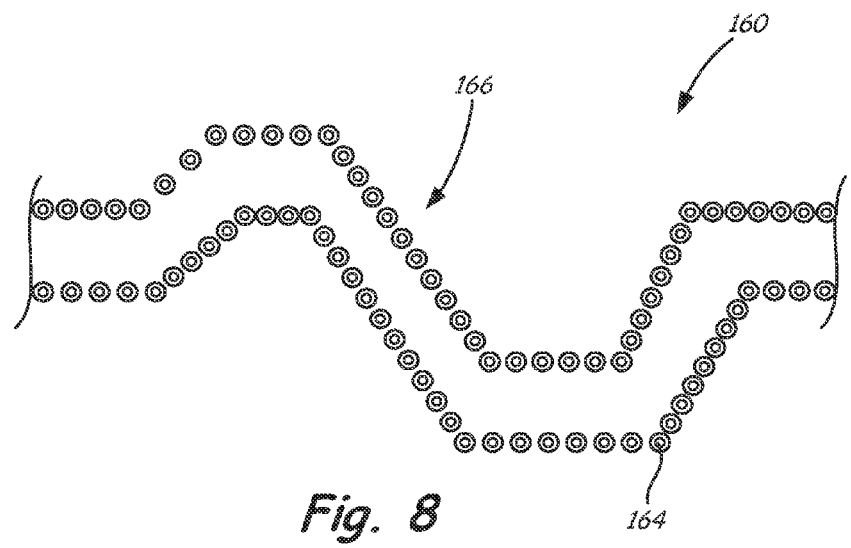
FIG. 8 is a schematic cross-sectional view of an implantable temporary lead including a conductive coil having a section that reshapes after implantation.

FIG. 8 is a schematic cross-sectional view of a portion of a temporary implantable medical device lead 160 according to another embodiment of the present disclosure. The lead 160 includes a conductor 164 having a fixation shape 166. While not specifically illustrated in FIG. 8, the lead 160 includes other elements similar to those described herein, such as a connector at the proximal end of the lead 160, and electrodes near a distal end of the lead 160.

The conductor 164 is configured to reshape after implantation such that the overall diameter or profile of the conductor 164 along the fixation shape 166 is larger than the diameter of the conductor 164 along other portions of the lead 160. More particularly, in the embodiment illustrated, the conductor 164 includes a fixation shape 166 having a substantial S-shape or wave shape that has a larger shape profile than other portions of the conductor 164 along the length of the lead 160. When in the expanded state, the fixation shape 166 provides an outward radial force on surrounding tissue, thereby facilitating fixation of the lead 160. In some embodiments, the fixation shape 166 is formed by winding the helically coiled conductor 164 around a mandrel or other device, or shaping the helically coiled conductor 164 into the desired fixation shape 166. The fixation shape 166 may have other shapes other than that illustrated, including, but not limited to, a spiral shape and a zig-zag shape. In some embodiments, the fixation shape 166 includes one or more electrodes.

During implantation, the fixation shape 166 is collapsed to provide a substantially uniform outer profile for the lead 160. In some embodiments, a stiff stylet is disposed in the lumen of the lead 160 to straighten the fixation shape 166. In other embodiments, the lead 160 (and fixation shape 166) are stretched axially to collapse the fixation shape 166. For example, the lead 160 may includes a distal lead cap such as those illustrated in FIGS. 6 and 7 coupled to a distal end of the conductor 164. A stylet may be manipulated to push the distal lead cap distally to stretch the fixation shape 166 into the collapsed position.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. For example, while the embodiments of the temporary implantable medical device leads described herein include particular lead structures, fixation mechanisms, and attachment methods, any of the lead structures and/or fixation mechanisms described or contemplated herein may be included in a lead in accordance with the present disclosure. Accordingly, the scope of the present disclosure is intended to embrace all such alternatives, modifications, and variations as fall within the scope of the claims, together with all equivalents thereof.

We claim:

1. A temporary implantable medical device lead comprising:
    a connector configured to connect the lead to an external control module;
    a helically coiled conductor having a proximal end mechanically and electrically connected to the connector, the helically coiled conductor including a plurality of insulated filars, the plurality of insulated filars insulated by a first polymer material that coats the filars;
    one or more electrodes defined by uninsulated portions of the helically coiled conductor; and
    one or more tine assemblies proximal to the one or more electrodes and configured to inhibit axial migration of the temporary implantable medical device lead, each tine assembly including a base and a plurality of tines extending from the base, each base formed from a second polymer material that is bonded with the first polymer material that coats the filars.

2. The temporary implantable medical device lead of claim 1, wherein a first outer diameter of the helically coiled conductor adjacent to each of the one or more tine assemblies is less than a second outer diameter of the helically coiled conductor along portions not adjacent to the one or more tine assemblies.

3. The temporary implantable medical device lead of claim 2, wherein a difference between the second outer diameter and the first outer diameter is up to twice a thickness of the one or more tines.

4. The temporary implantable medical device lead of claim 1, wherein at least one of the one or more tine assemblies is configured to prevent distal axial migration of the temporary implantable medical device lead.

5. The temporary implantable medical device lead of claim 1, wherein the first polymer material that coats the filars is thermally fused to the second polymer of each base.

6. The temporary implantable medical device lead of claim 1, and further comprising:

a distal tine assembly disposed at a distal end of the helically coiled conductor distal to the one or more electrodes and configured to inhibit radial movement of the lead.

7. The temporary implantable medical device lead of claim 1, wherein the helically coiled conductor includes one or more preformed sections that are collapsible during implantation and that increase an outer diameter of the temporary implantable medical device lead after implantation.

8. The temporary implantable medical device lead of claim 7, and further comprising:
one or more electrodes on each of the one or more preformed sections.

9. The temporary implantable medical device lead of claim 7, and further comprising:
a distal lead cap coupled to a distal end of the helically coiled conductor, wherein the distal lead cap includes a slot configured to receive an implantation tool to collapse the preformed section during implantation.

10. The temporary implantable medical device lead of claim 1, and further comprising:
a shape memory element coextending with a portion of the helically coiled conductor, the shape memory element collapsible to a position adjacent to the helically coiled conductor during implantation and expandable to a diameter greater than an outer diameter of the helically coiled conductor after implantation.

11. A temporary implantable medical device lead comprising:
a connector configured to connect the lead to an external control module;
a helically coiled conductor having a proximal end mechanically and electrically connected to the connector, the helically coiled conductor including a plurality of insulated filars, wherein the helically coiled conductor includes one or more preformed sections that are collapsible during implantation and that increase an outer diameter of the temporary implantable medical device lead after implantation; and
one or more electrodes defined by uninsulated portions of the helically coiled conductor.

12. The temporary implantable medical device lead of claim 11, and further comprising:
a distal lead cap coupled to a distal end of the helically coiled conductor, wherein the distal lead cap includes a slot configured to receive an implantation tool to collapse the preformed section during implantation.

13. The temporary implantable medical device lead of claim 11, wherein at least one of the one or more preformed sections comprises a flare in the helically coiled conductor.

14. The temporary implantable medical device lead of claim 11, and further comprising:
one or more electrodes on each of the one or more preformed sections.

15. The temporary implantable medical device lead of claim 11, and further comprising:
one or more tine assemblies configured to inhibit axial migration of the temporary implantable medical device lead, each tine assembly including a base and a plurality of tines extending from the base, wherein a first outer diameter of the helically coiled conductor adjacent to each of the one or more tine assemblies is less than a second outer diameter of the helically coiled conductor along portions not adjacent to the one or more tine assemblies.

16. The temporary implantable medical device lead of claim 15, wherein a difference between the second outer diameter and the first outer diameter is up to twice a thickness of the one or more tines.

17. The temporary implantable medical device lead of claim 15, wherein at least one of the one or more tine assemblies is configured to prevent distal axial migration of the temporary implantable medical device lead.

18. A system comprising:
an externally carried control module; and
a temporary implantable medical device lead including:
a connector configured to connect the lead to the control module; and
a helically coiled conductor having a proximal end mechanically and electrically connected to the connector, the helically coiled conductor including a plurality of insulated filars, the helically coiled conductor defining a lumen;
one or more electrodes defined by uninsulated portions of the helically coiled conductor; and
one or more tine assemblies proximal to the one or more electrodes and configured to inhibit axial migration of the temporary implantable medical device lead, each tine assembly including a base and a plurality of tines extending from the base, the base at least partially located within the lumen.

19. The system of claim 18, wherein a first outer diameter of the helically coiled conductor adjacent to each of the one or more tine assemblies is less than a second outer diameter of the helically coiled conductor along portions not adjacent to the one or more tine assemblies.

20. The system of claim 19, wherein a difference between the second outer diameter and the first outer diameter is approximately equal to a width of the one or more tines.

21. The system of claim 18, wherein at least one of the one or more tine assemblies is configured to prevent distal axial migration of the temporary implantable medical device lead.

* * * * *